United States Patent [19]

Crouse

[11] Patent Number: 5,324,302
[45] Date of Patent: Jun. 28, 1994

[54] LANCET WITH LOCKING COVER

[75] Inventor: Roger L. Crouse, Ormond Beach, Fla.

[73] Assignee: Sherwood Medical Company, St. Louis, Mo.

[21] Appl. No.: 960,074

[22] Filed: Oct. 13, 1992

[51] Int. Cl.$^5$ ............................................. A61B 17/32
[52] U.S. Cl. ................................... 606/181; 606/167
[58] Field of Search ............... 604/115, 117, 158, 162, 604/171; 606/167, 172, 181, 182, 183, 184, 185

[56] References Cited

U.S. PATENT DOCUMENTS

| | | |
|---|---|---|
| 3,338,239 | 8/1967 | Mausteller . |
| 3,358,689 | 12/1967 | Higgins . |
| 3,902,489 | 9/1975 | Carter . |
| 4,388,925 | 6/1983 | Burns . |
| 4,416,279 | 11/1983 | Lindner et al. . |
| 4,425,120 | 1/1984 | Sampson et al. . |
| 4,494,543 | 1/1985 | Hart . |
| 4,503,856 | 3/1985 | Cornell et al. . |
| 4,573,976 | 3/1986 | Sampson et al. . |
| 4,580,565 | 4/1986 | Cornell et al. . |
| 4,635,633 | 1/1987 | Hufnagle . |
| 4,655,751 | 4/1987 | Harbaugh . |
| 4,676,244 | 6/1987 | Enstrom . |
| 4,712,548 | 12/1987 | Enstrom . |
| 4,723,943 | 2/1988 | Spencer . |
| 4,735,618 | 4/1988 | Hagen . |
| 4,738,261 | 4/1988 | Enstrom . |
| 4,752,290 | 6/1988 | Schramm . |
| 4,758,231 | 7/1988 | Haber et al. . |
| 4,767,413 | 8/1988 | Haber et al. . |
| 4,787,891 | 11/1988 | Levin et al. . |
| 4,867,172 | 9/1989 | Haber et al. . |
| 4,869,249 | 9/1989 | Crossman et al. . |
| 4,889,117 | 12/1989 | Stevens . |
| 4,898,589 | 2/1990 | Dolgin et al. . |
| 4,935,013 | 6/1990 | Haber et al. . |
| 4,950,250 | 8/1990 | Haber et al. . |
| 4,976,724 | 12/1990 | Nieto et al. . |
| 5,014,718 | 5/1991 | Mitchen . |
| 5,047,016 | 9/1991 | Dolgin et al. . |
| 5,071,426 | 12/1991 | Dolgin et al. . |
| 5,108,379 | 4/1992 | Dolgin et al. . |
| 5,133,730 | 7/1992 | Biro et al. . |

OTHER PUBLICATIONS

PCT WO91/08712, Jun. 27, 1991, Sunmo.
EPA O 137975, Apr. 25, 1985, Nitzsche et al.

*Primary Examiner*—John D. Yasko
*Assistant Examiner*—N. Kent Gring
*Attorney, Agent, or Firm*—Andrew J. Beck; Montgomery W. Smith; Curtis D. Kinghorn

[57] ABSTRACT

A blood lancet is disclosed having a lancet needle with a sharpened lancet tip. The lancet tip is covered before use. The lancet tip end of the lancet needle extends through a slidable proximal needle piece while the opposite end of the lancet needle is immovably embedded in a distal needle piece. The distal needle piece is connected to the proximal needle piece through a pair of opposed normally bowed flexible arms. After pricking the user's skin with the lancet tip, the bowed flexible arms are pinched towards each other which pushes the proximal needle piece into a position over and enclosing the lancet tip. The flexible arms each have an arrow shaped protrusion or catch that engages a correspondingly shaped receptacle on the distal needle piece to lock the proximal needle piece in position over the lancet tip. In one embodiment, a removable cap covers the lancet tip. In another embodiment, the proximal needle piece is formed around the lancet tip. In this embodiment, the lancet is pinched along the length of the lancet needle thereby pushing the lancet tip through the proximal needle piece into the user's finger.

39 Claims, 4 Drawing Sheets

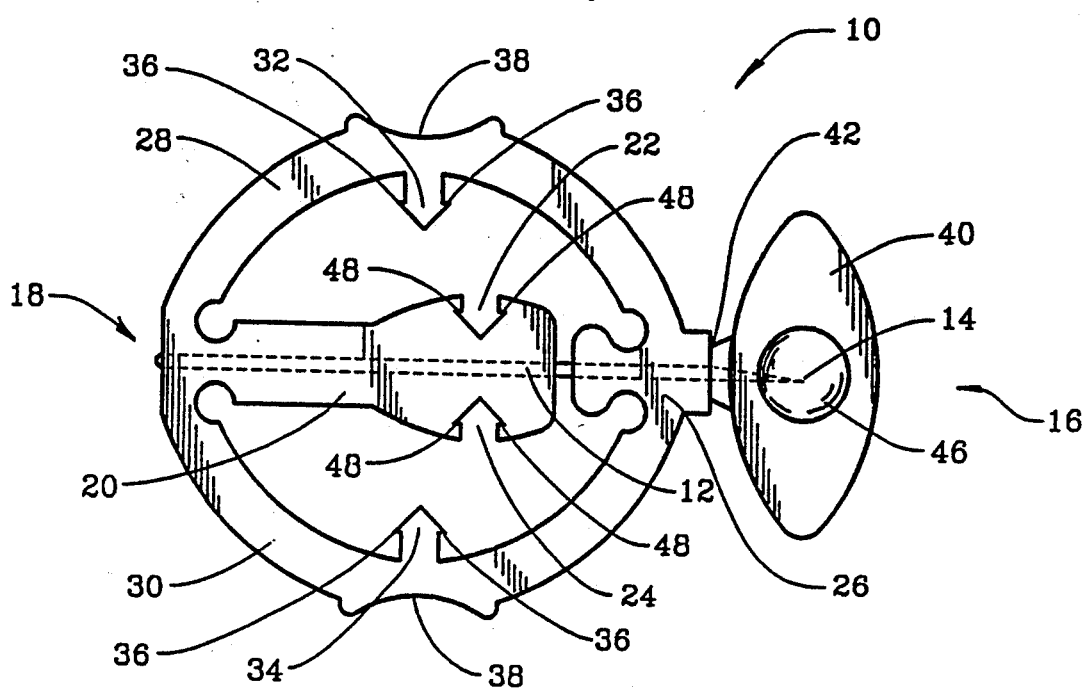
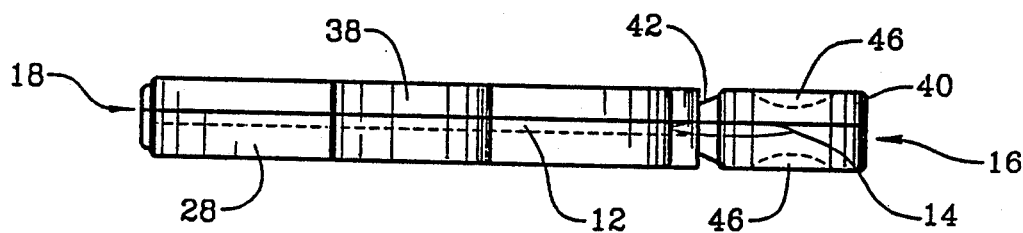
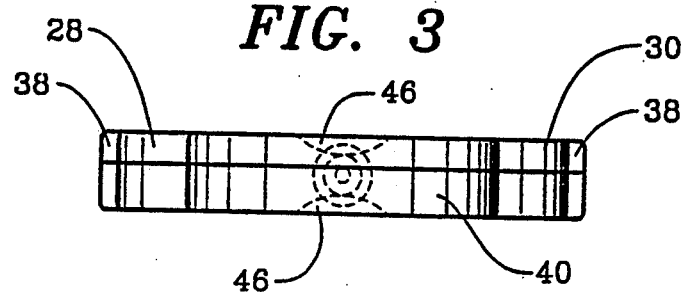

LANCET WITH LOCKING COVER

BACKGROUND OF THE INVENTION

1. Field of the Invention

The invention relates to lancets and more particularly to a blood lancet with a protective movable cover for the lancet tip that is lockable into a tip covering position.

2. Description of Related Art

Many patient illnesses, such as diabetes, require the patient to take a small sample of blood for analysis purposes. Typically, this blood sample is obtained by pricking the patient's skin so that a drop of blood is produced. The patient's skin is typically pricked by means of a lancet. Originally these lancets consisted of a sharp pointed object that was manually pushed through the patient's skin creating a small wound through which the blood drop would flow.

A problem with such lancets is that the sharp lancet tip, after piercing the patient's skin, is exposed and therefore able to accidentally reprick the patient or others. For this reason, lancets having caps that cover the exposed lancet tip before use have been developed. In these devices, the cap may be replaced over the lancet tip after use to prevent inadvertent contact with the sharpened lancet tip. Examples of such devices are U.S. Pat. No. 3,358,689 issued to J. L. Higgins on Dec. 19, 1967; U.S. Pat. No. 4,635,633 issued to D. R. Hufnagle on Jan. 13, 1987; and, U.S. Pat. No. 4,712,548 issued to H. Enstrom on Dec. 15, 1987.

A problem with these devices is that, although the lancet tip is covered by the cap when it is in place, the lancet tip is exposed if the cap is inadvertently dislodged from its protective place. Consequently, it is desirable produce a lancet having a lancet tip that is not exposed after use and that may not be inadvertently exposed after use.

Another approach to preventing accidental contact with the sharpened lancet tip has been to bias the lancet tip in a non-exposed position before and after use. The bias is usually accomplished by means of a spring. When the patient desires to draw a sample of blood, the bias of the lancet tip is overcome thereby exposing the lancet tip which contacts the patient's skin so that a drop of blood may be drawn. Thereafter, the bias moves the needle into a retracted position. Examples of this type of blood lancet are U.S. Pat. No. 3,338,239 issued to J. W. Mausteller on Aug. 29, 1967; U.S. Pat. No. 4,503,856, and U.S. Pat. No. 4,580,565, issued to Cornell et al. on Mar. 12, 1985, and Apr. 8, 1986 respectively; U.S. Pat. Nos. 4,676,244 and 4,738,261 issued to H. Enstrom on Jun. 30, 1987 and Apr. 19, 1988, respectively; and, U.S. Pat. No. 4,976,724 issued to R. L. Nieto et al. on Dec. 11, 1990.

A problem with this type of device is that the devices are relatively complicated and difficult to manufacture. In view of this, it is desirable to produce a lancet that is relatively simple and inexpensive to manufacture.

Another problem with these devices is that, although the lancet tip is retracted before and after use, after use, the lancet tip may inadvertently be re-exposed by inadvertently overcoming the bias holding the lancet tip in the retracted position. When the lancet tip is re-exposed, inadvertent contact may occur. This is a situation to be avoided.

SUMMARY OF THE INVENTION

A blood lancet is provided having a lancet needle with a sharpened lancet tip. The lancet tip is covered before use. The lancet tip end of the lancet needle extends through a slidable proximal needle piece while the opposite end of the lancet needle is immovably embedded in a distal needle piece. The distal needle piece is connected to the proximal needle piece through a pair of opposed normally bowed flexible arms. In the preferred embodiment, the flexible arms are bowed to position the proximal needle piece so that the lancet tip extends beyond the proximal end of the proximal needle piece and is therefore exposed. A removable cap is formed over the lancet tip during manufacture. To use the lancet device, the cap is removed, thereby exposing the lancet tip.

After pricking the user's skin with the lancet tip, the bowed flexible arms are pinched towards each other which pushes the proximal needle piece into a position over and enclosing the lancet tip. The flexible arms each have an arrow shaped protrusion or catch that engages a correspondingly shaped receptacle on the distal needle piece to lock the proximal needle piece in position over the lancet tip.

In an alternate embodiment, the lancet tip is formed in the proximal needle piece so that it does not extend beyond the proximal end of the proximal needle piece as in the preferred embodiment. At the time a blood sample is to be taken, the user pinches the proximal and distal needle pieces together between the user's thumb and finger. This moves the lancet tip beyond the proximal end of the proximal needle piece and into contact with the user's finger. Thereafter, the bowed flexible arms are pinched together which moves the proximal needle piece over the lancet tip to prevent inadvertent contact with the lancet tip. This embodiment also includes protrusions or catches extending from the arms and receptacles in the distal needle piece, as described above, that interact to lock the proximal needle piece over the lancet tip.

It is therefore an object of the invention to provide a lancet device that covers the lancet tip after use.

It is another object of the invention to provide a lancet device that locks the cover of the lancet tip over the lancet tip after use so that the lancet tip may not thereafter inadvertently be exposed.

It is another object of the invention to produce a lancet device that is relatively simple to manufacture.

It is another object of the invention to produce a lancet device that is relatively small.

These and other objects of the invention will be clear from the description contained herein and more particularly with reference to the following detailed description and the attached drawings where like elements are referred to by like reference numbers.

BRIEF DESCRIPTION OF THE DRAWINGS

FIG. 1 is a side elevational view of the lancet device of the invention with the protective cap in place.

FIG. 2 is a top view of the device in FIG. 1.

FIG. 3 is an end view of the device of FIG. 1 as viewed from the side of the device containing the protective cap.

DETAILED DESCRIPTION OF THE INVENTION

Figure 4:
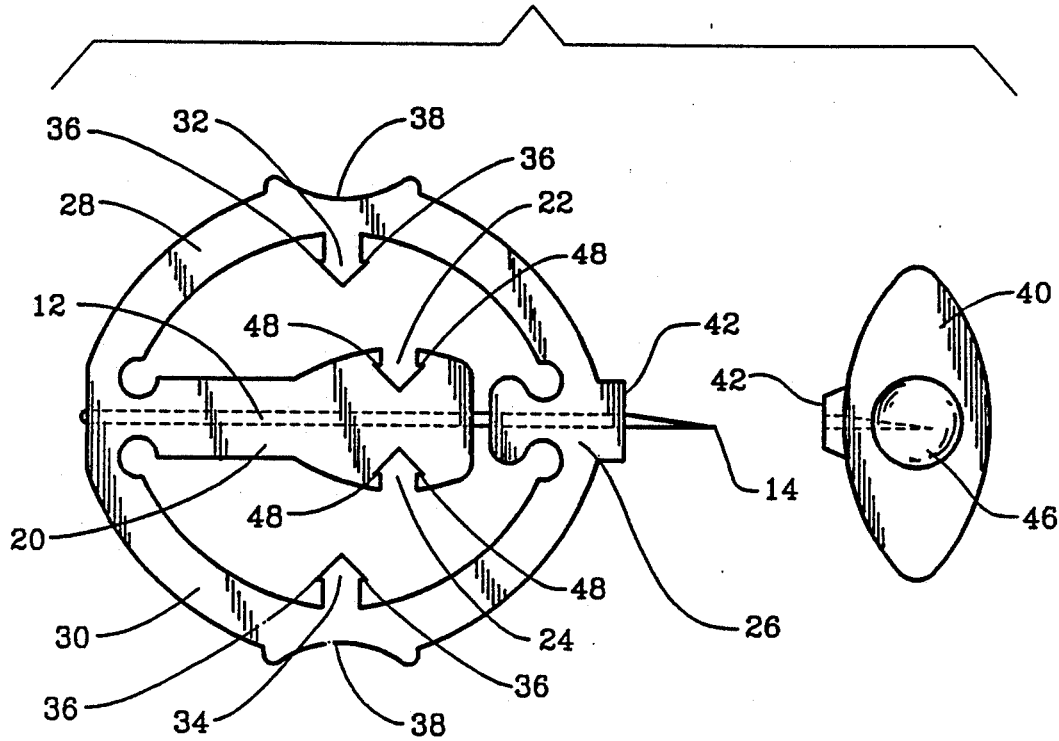
FIG. 4 is a side elevational view of the device of FIG. 1 with the cap removed from the device thereby exposing the sharpened lancet tip.

Referring to FIG. 1, the lancet device is shown generally labeled 10. Lancet device 10 has a proximal or patient contacting end generally labeled 16 and a distal end generally labeled 18. The device 10 includes a lancet needle 12 having a lancet tip 14 at the proximal end. In the preferred embodiment, lancet needle 12 is about 0.031" in diameter and about one inch long.

The distal end of lancet needle 12 is encased in a distal needle piece 20. In FIG. 1, lancet needle 12 is shown in dotted lines encased in distal needle piece 20. Distal needle piece 20 encloses a significant length of lancet needle 12. In the preferred embodiment, distal needle piece 20 is molded around lancet needle 12 to enclose more than half the length of lancet needle 12.

Distal needle piece 20 includes a pair of opposed receptacles 22, 24 extending into distal needle piece 20 on opposite sides of lancet needle 12 at approximately right angles to lancet needle 12. Receptacles 22, 24 will be described in more detail hereafter.

A proximal neeale piece 26 is spaced away from and located proximal to distal needle piece 20 along lancet needle 12. In manufacture, proximal needle piece 26 is molded to enclose and encase a portion of lancet needle 12. The length of lancet needle 12 encased by proximal needle piece 26 is preferably considerably smaller than the portion of lancet needle 12 encased by distal needle piece 20 for a purpose that will be described hereafter. In the preferred embodiment, the length of lancet needle 12 enclosed by proximal needle piece 26 is approximately one fourth the length of lancet needle 12 enclosed by distal needle piece 20.

A pair of arms 28,30 connect Of distal needle piece 20 with proximal needle piece 26 along opposite sides of lancet needle 12. Arms 28,30 are relatively thin and flexible. In the preferred embodiment, arms 28,30 extend from the distal end of distal needle piece 20 to the proximal end of proximal needle piece 26. In this way, the overall length of lancet device 10 is minimized.

Each arm 28,30 has a catch 32,34 respectively, extending from arm 28,30 inwardly toward lancet needle 12. In the preferred embodiment, catches 32,34 are arrow shaped so that a pair of edges 36 extend away from each catch 32,34 respectively. In a variation of the shape of catches 32,34, catches 32,34 may be conical shaped so that a single annular ridge extends around catches 32,34. Receptacles 22,24 are shaped to correspond to the shape of the catches 32,34.

Each arm 28,30 preferably has a finger pad 38 on the outer surface of each arm 28,30 directed away from lancet needle 12. Finger pads 38 are preferably cup shaped to allow arms 28,30 to be more easily grasped between the fingers of the user as will be explained hereafter. Finger pads 38 may, in addition or in the alternative, include a friction producing surface such as a cross-hatched or rough surface to prevent the user's fingers from slipping off of finger pads 38.

A cap 40 encloses lancet tip 14. During manufacture, cap 40 is preferably integrally molded with proximal needle piece 26 and is formed around and encloses lancet tip 14. A thin piece of plastic connects cap 40 to proximal needle piece 26 at breakoff point 42 at the proximal end of proximal needle piece 26. In the preferred embodiment, the thickness of the plastic at breakoff point 42 is about 0.010" and extends entirely around lancet needle 12.

As stated, during manufacture cap 40 is preferably integrally made with proximal needle piece 26. In this way, cap 40 makes a seal with proximal needle piece 26 at breakoff point 42 so that lancet tip 14 is totally encapsulated within cap 40 to preserve the sterility of lancet tip 14 after the manufacturing process.

Cap 40 also includes a pair of opposed cap finger pieces 46 (FIG. 2) that allow cap 40 to be grasped. In the preferred embodiment, finger pieces 46 are concave extending into cap 40 from opposed sides. In addition or in the alternative, finger pieces 46 may also include a friction producing surface as a cross-hatched or rough surface to prevent the user's fingers from slipping off of finger pieces 46.

In use, cap 40 is removed from its contact with proximal needle piece 26. This is best done by the user grasping device 10 by finger pads 38, preferably between the forefinger A and thumb B of one hand. Thereafter, cap 40 is grasped between the thumb and forefinger of the other hand pinching cap finger pieces 46. Cap 40 is twisted relative to proximal needle piece 26. At this time, the thin plastic connection at breakoff point 42 is broken so that cap 40 may be removed from proximal needle piece 26 as shown in FIG. 4. When cap 40 is removed from proximal needle piece 26, lancet tip 14 is exposed (FIG. 4).

Figure 5:
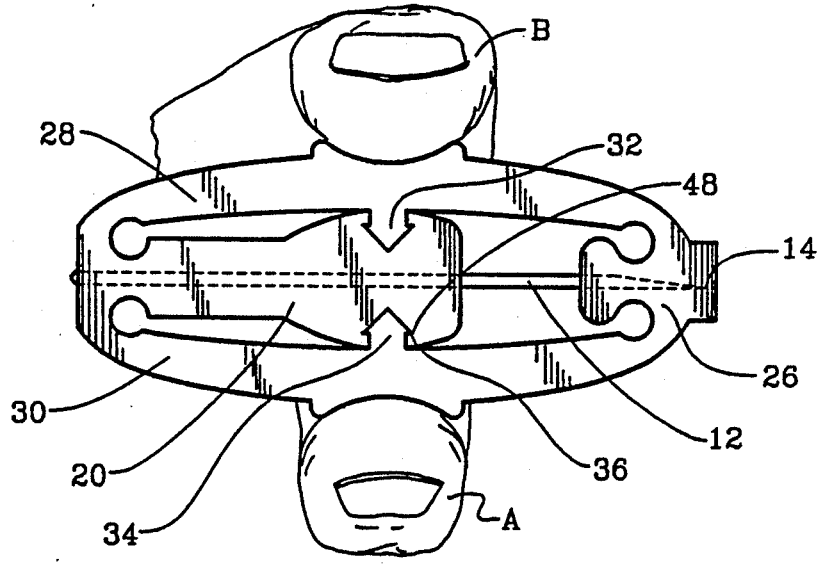
FIG. 5 is a side elevational view of the device of FIG. 1 grasped between a user's thumb and forefinger to place the device in its protective locked position.
Figure 6:
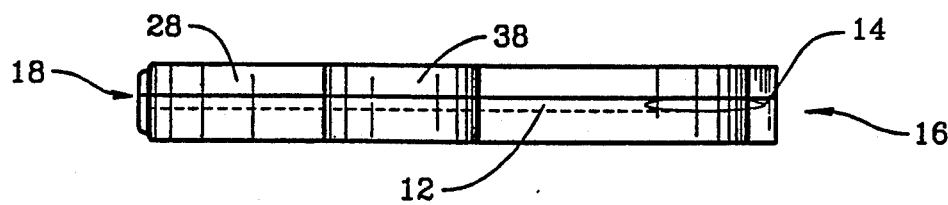
FIG. 6 is a top view of the device of FIG. 1 in its locked configuration as shown in FIG. 5.

With lancet tip 14 exposed, the user may move lancet tip 14 into contact with the skin so that a drop of blood may be drawn. Thereafter, in order to cover lancet tip 14, proximal needle piece 26 is moved over lancet tip 14. Proximal needle piece 26 is moved over lancet tip 14 by pinching arms 28,30 together between finger pads 38 as shown in FIG. 5. As arms 28,30 are pinched together, pressure is placed on distal needle piece 20 and proximal needle piece 26 to move away from each other. Because, in the preferred embodiment, the surface area of proximal needle piece 26 in contact with lancet needle 12 is considerably less than the surface area contacting lancet needle 12 within distal needle piece 20, about one fourth the length, proximal needle piece 26 will break loose from its frictional contact with lancet needle 12 and move proximally away from distal needle piece 20. As proximal needle piece 26 moves away from distal needle piece 20, proximal needle piece 26 moves over and encloses lancet tip 14 as shown in FIG. 5.

As arms 28,30 are pinched towards each other, catches 32,34 are moved into contact with receptacles 22,24 respectively. As catches 32,34 are moved farther into receptacles 22,24, the material along the sides of receptacles 22,24 deforms around ridges 36 to allow catches 32,34 to move farther into receptacles 22,24. When catches 32,34 are moved farthest into receptacles 22,24, ridges 36 move into contact with the correspondingly shaped recesses 48 to securely hold catches 32,34 within receptacles 22,24. Because catches 32,34 are securely held or "locked" into receptacles 22,24 respectively, proximal needle piece 26 is "locked" into position enclosing lancet tip 14, thereby preventing inadvertent contact with lancet tip 14.

As described above, arms 28,30 preferably extend from the distal end of distal needle piece 20 to the proximal end of proximal needle piece 26. However, the invention will work with arms 28,30 attached to distal needle piece 20 and proximal needle piece 26 at any point along their respective surfaces parallel to lancet needle 12 so long as catches 32,34 may engage receptacles 22,24 as described above.

Figure 7:
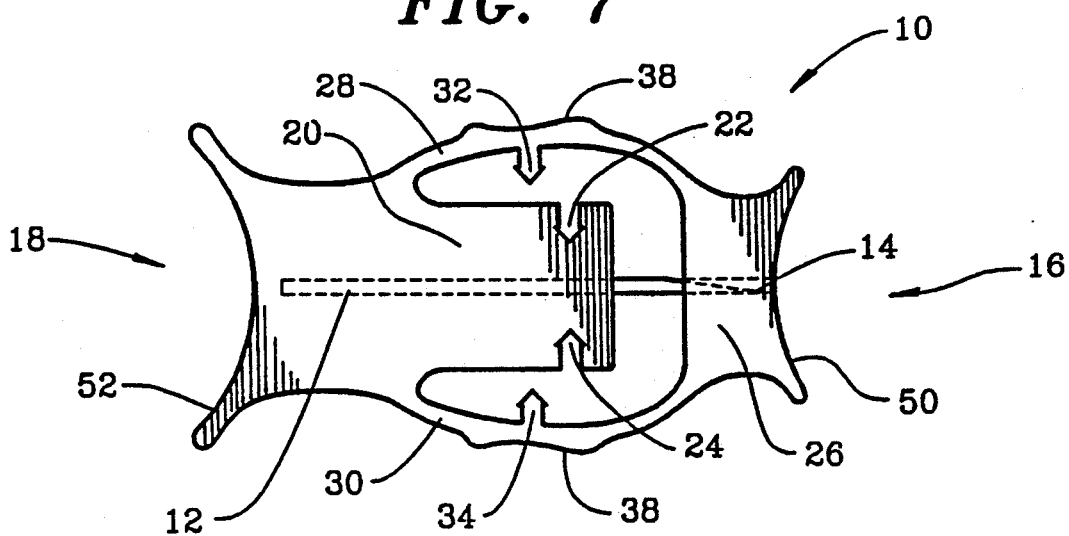
FIG. 7 is a side elevational view of an alternate embodiment of the invention.
Figure 8:
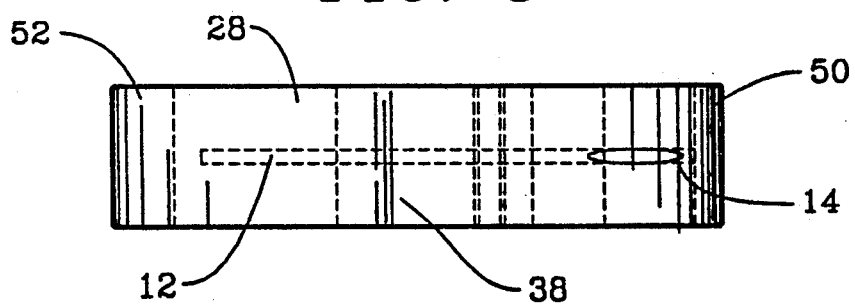
FIG. 8 is a top view of the device of FIG. 7.
Figure 9:
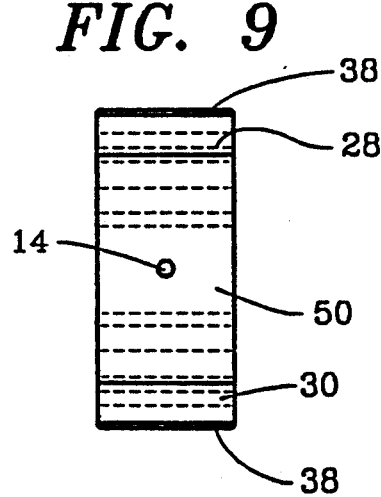
FIG. 9 is an end view of the device of FIG. 7.

FIG. 7 shows an alternate embodiment of the invention described above. Similar elements in both embodiments are referred to by similar reference numbers. In the embodiment shown in FIG. 7, lancet tip 14, instead of extending proximally beyond proximal needle piece 26, as in the embodiment of FIG. 1, is, upon manufacture, contained within proximal needle piece 26. In addition, a proximal and a distal finger pad 50,52, respectively, are placed on the proximal end of proximal needle piece 26 and the distal end of distal needle piece 20. In this embodiment, there is no cap 40. In all other ways, the embodiment resembles the embodiment shown in FIG. 1.

Figure 10:
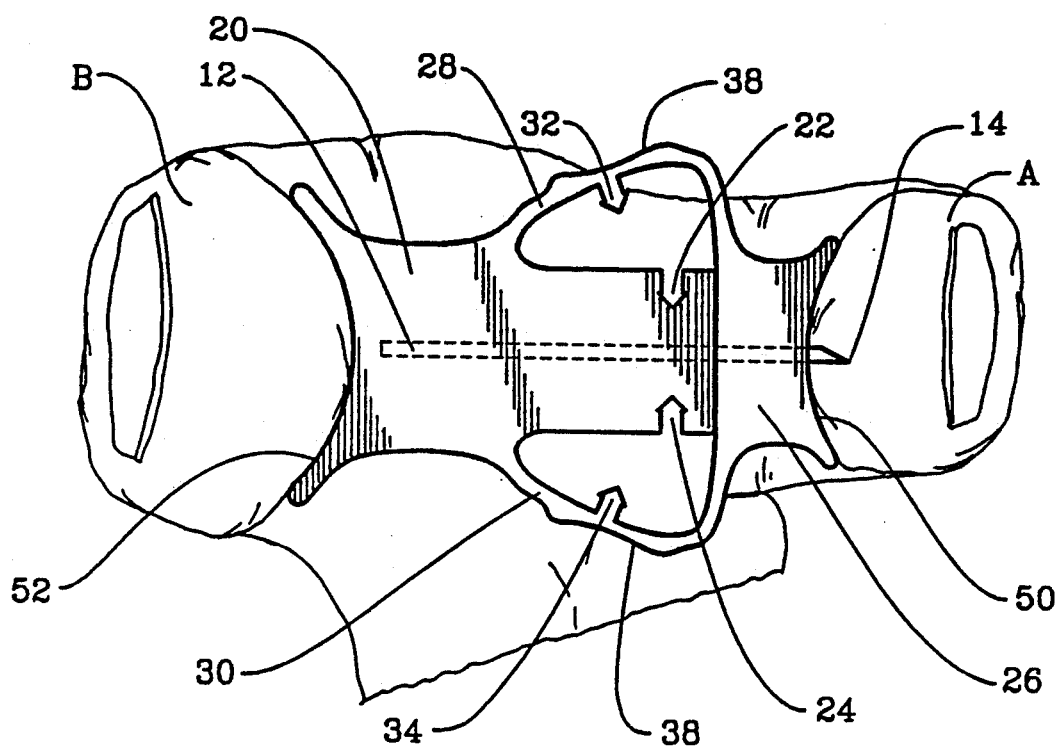
FIG. 10 is a side elevational of the device of FIG. 7 in position between a user's thumb and finger showing the device of FIG. 1 with the lancet tip penetrating the user's skin.
Figure 11:
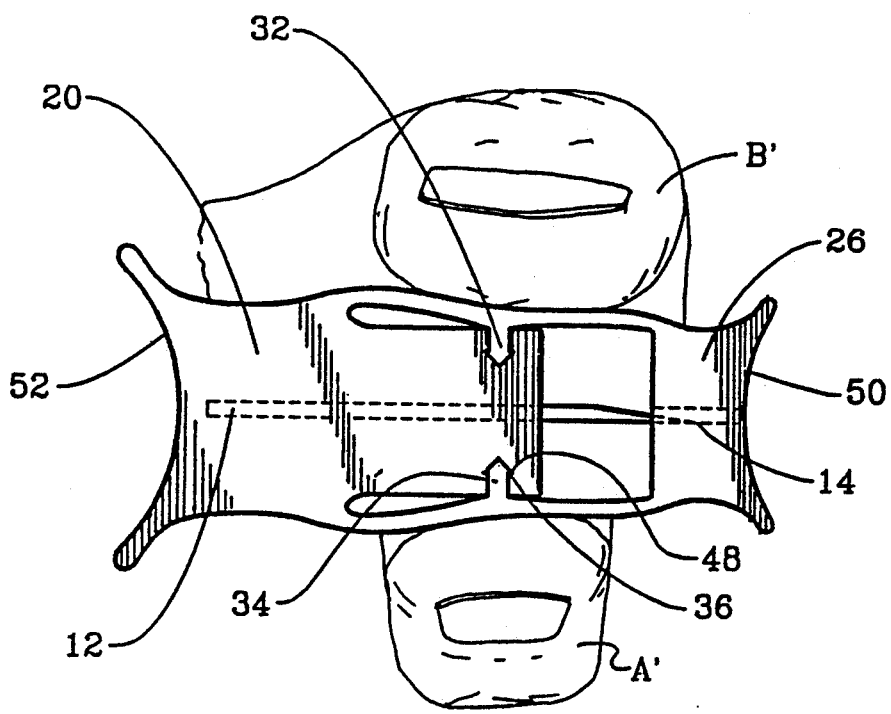
FIG. 11 is a side elevational view of the device of FIG. 7 shown pinched between the user's thumb and forefinger thereby placing the device in its closed and locked position.

In operation, the user grasps the device 10 between his forefinger A and thumb B at proximal finger pad 50 and distal finger pad 52 as shown in FIG. 10. As the user squeezes, the contact with the finger A and proximal finger pad 50 causes proximal needle piece 26 to move toward distal needle piece 20 thereby moving lancet tip 14 beyond the proximal end of proximal finger pad 50 into contact with the user's finger A. This contact between lancet tip 14 and the user's finger A causes a puncture in the user's finger A that allows a drop of blood to be taken. Thereafter, the user grasps arms 28,30 at finger pads 38 between finger A' and thumb B' and pinches arms 28,30 together forcing receptacles 22,24 into locking contact with catches 32,34 as described above (FIG. 11). This causes lancet tip 14 to move back around and enclose proximal needle piece 26 as shown in FIG. 11. The interaction between catches 32,34 and receptacles 22,24 "locks" proximal needle piece 26 into position around lancet tip 14.

In both embodiments shown, distal needle piece 20, proximal needle piece 26 and arms 28,30 are preferably made of a flexible plastic material such as polyethylene. The material has sufficient stiffness to allow arms 28,30 to be pressed together while exerting pressure on proximal needle piece 26 to move proximally away from distal needle piece 20. Preferably, the plastic material is molded around lancet needle 12 by techniques well understood in the art. However, distal needle piece 20, proximal needle piece 26 and arms 28,30 may also be molded first and lancet needle 12 inserted into position later.

In the embodiments shown, proximal needle piece 26 is molded around lancet needle 12 and contacts needle 12 along a relatively smaller distance than distal needle piece 20 contacts lancet needle 12. This allows proximal needle piece 26 to break loose from its frictional contact with lancet needle 12 before distal needle piece 20 will break loose from frictional contact with lancet needle 12 when arms 28,30 are pinched together. However, in a variation of these embodiments, lancet needle 12 may have a lubricous coating applied along the area where proximal needle piece 26 will move to aid in proximal needle piece 26 breaking its frictional contact with lancet needle 12. In the alternative or in addition, the surface of lancet needle 12 where proximal needle piece 26 will move may be provided with a much smoother, and consequently less friction producing surface, than the rest of lancet needle 12, particularly the part of lancet needle 12 embedded in distal needle piece 20.

In these embodiments, the length of proximal needle piece 26 surrounding lancet needle 12 need not vary greatly from the length of distal needle piece 20 in contact with lancet needle 12. When arms 28,30 are pinched together, proximal needle piece 26 will more easily slide along lancet needle 12 as described above.

In another alternate embodiment, distal needle piece 20, proximal needle piece 26, and arms 28,30 may be molded at one time and lancet needle 12 inserted into position later. In this embodiment, proximal needle piece 26 may be manufactured with a bore extending through it through which lancet needle 12 will extend. This bore has a diameter slightly larger than the diameter of lancet needle 12. After lancet needle 12 is positioned in distal needle piece 20 and extends through proximal needle piece 26, when arms 28,30 are pinched together, proximal needle piece 26 will slide along lancet needle 12 as described above.

In the embodiments described above, catches 32,34 extend from arms 28,30 toward lancet needle 12 while recesses 22,24 extend into distal needle piece 20. This configuration may be reversed so that catches, corresponding in shape to catches 32,34, extend away from distal needle piece 20 toward arms 28,30 and are retained in recesses, corresponding in shape to recesses 22,24, extending into arms 28,30.

In all the embodiments and variations thereof described above, the specific shape of the catches 32,34 and receptacles 22,24 may be varied from the "arrow" and conical shapes described herein to other shapes such as spherical or half-spherical, to name but a few of the possibilities. The key to the shapes of catches 32,34 and receptacles 22,24 is that catches 32,34 are securely retained within receptacles 22,24 once catches 32,34 are placed within receptacles 22,24. Consequently, any shape for catches 32,34 and receptacles 22,24 that performs this intended function is within the scope of the invention. Further, the shapes for distal needle piece 20, proximal needle piece 26, finger pads 38, and proximal and distal finger pads 50,52, among other pieces described herein, may be varied so long as the elements perform their respective functions as described above.

Further, specific dimensions have been given for the lancet needle 12. These dimensions have been given for the purpose of illustration and not for limiting the scope of the disclosure. Lancet needles of other sizes and relative dimensions may be used in the invention as desired.

The invention has been described in connection with specific embodiments. However, the disclosure given herein is intended for the purpose of illustration and not for the purpose of limitation. Changes and modifications may be made to the description contained herein and still be within the scope of the invention. Further, obvious changes and modifications will occur to those skilled in the art.

What is claimed is:

1. A lancet device comprising:
a) a lancet needle having a distal and a proximal end, said proximal end of said lancet needle having a sharpened tip;
b) a distal needle piece encasing said distal end of said lancet needle;
c) a proximal needle piece enclosing a portion of said lancet needle at said proximal end of said lancet needle, said proximal needle piece enclosing said lancet needle along less of said lancet needle than said distal needle piece encases said lancet needle;
d) a pair of opposed bowed flexible arms connecting said distal needle piece to said proximal needle piece along opposite sides of said lancet needle, said arms having a rigidity so that as said arms are moved towards each other pressure is exerted by said arms on said distal needle piece and said proximal needle piece to move said proximal needle piece away from said distal needle piece along said lancet needle to a position to cover and enclose said lancet tip;
e) means for locking said proximal needle piece in a position covering and enclosing said lancet tip, said means for locking including said arms having at least one means for contacting said distal needle piece when said arms are moved toward said distal needle piece and said distal needle piece having means for retaining said means for contacting to lock said corresponding arms in contact with said distal needle piece thereby locking said proximal needle piece in position over said lancet tip, said means for contacting comprising a protrusion extending from said arms towards said lancet needle and said means for retaining including said distal needle piece having a deformable recess in corresponding shape to said protrusion so that said protrusion is moved into said recess as said arms are moved toward said lancet needle and said recess deforms around said protrusion to retain said protrusion therein;
f) a proximal finger pad attached to the proximal end of said proximal needle piece and a distal finger pad attached to said distal end of said distal needle piece;
g) a pair of finger pads attached to the outer surface of said arms opposite said lancet needle to allow said arms to be grasped and pinched between fingers of a user's hand towards said lancet needle.

2. A lancet device comprising:
a) a lancet needle having a distal and a proximal end, said proximal end of said lancet needle having a sharpened tip;
b) means for enclosing a portion of said lancet needle at said proximal end of said lancet needle; and
c) at least a pair of arms, each arm attached at one end to said distal end of said lancet needle and attached at an opposed end to said means for enclosing, said arms having a center section between said distal end of said lancet needle and said means for enclosing, said arms having a bowed shape in a relaxed condition so that said center section is relatively farther away from said lancet needle than the portions of said arms attached to said distal end of said lancet needle and attached to said means for enclosing, said arms, in said relaxed condition, having a length to cause said sharpened tip to extend proximally beyond the proximal end of said means for enclosing; and, d) means, located at said center section, for receiving force directed toward said lancet needle;
whereby, as force is applied to said means for receiving force directed toward said lancet needle, said arms approach a straight shape as said center section is moved toward said lancet needle thereby exerting pressure by said arms on said means for enclosing to move said means for enclosing away from said distal end of said lancet needle to a position to cover and enclose said lancet tip.

3. The lancet device of claim 2 wherein said arms are attached to said distal end of said lancet needle by a distal needle piece.

4. The lancet device of claim 2 wherein said means for enclosing comprises a proximal needle piece.

5. The lancet device of claim 2 wherein the number of said arms is two and said arms are opposed across the lancet needle.

6. The lancet device of claim 2 wherein:
said arms are attached to said distal end of said lancet needle by a distal needle piece; and,
said means for enclosing comprises a proximal needle piece.

7. The lancet device of claim 6 wherein said distal needle piece encloses a portion of said distal end of said lancet needle.

8. The lancet device of claim 7 wherein said proximal needle piece encloses said lancet needle along less of said lancet needle than said distal needle piece encloses said lancet needle.

9. The lancet device of claim 2 further comprising means for locking said means for enclosing in a position covering and enclosing said lancet tip.

10. The lancet device of claim 9 wherein said means for locking includes said means for connecting having at least one means for contacting said means for positioning when said means for connecting are moved toward said means for positioning and said means for positioning having means for retaining said means for contacting to lock said corresponding means for connecting in contact with said means for positioning thereby locking said means for enclosing in position over said lancet tip.

11. The lancet device of claim 10 wherein said means for contacting comprises a protrusion extending from said means for connecting towards said lancet needle and wherein said means for retaining includes said means for positioning having a defomable recess in corresponding shape to said protrusion so that said protrusion is moved into said recess as said means for connecting are moved toward said lancet needle and said recess defoms around said protrusion to retain said protrusion therein.

12. The lancet device of claim 9 wherein said means for locking includes said means for positioning having at least one means for contacting said means for connecting when said means for connecting are moved toward said means for positioning and said means for connecting having means for retaining said means for contacting to lock said corresponding means for positioning in contact with said means for connecting thereby locking said means for enclosing in position over said lancet tip.

13. The lancet device of claim 12 wherein said means for contacting comprises a protrusion extending from said means for positioning away from said lancet needle and wherein said means for retaining includes said means for connecting having a deformable recess in corresponding shape to said protrusion so that said protrusion is moved into said recess as said means for connecting are moved toward said lancet needle and said recess deforms around said protrusion to retain said protrusion therein.

14. The lancet device of claim 2 further comprising a removable cap encasing and enclosing said lancet tip.

15. The lancet device of claim 14 wherein said cap is integrally attached to said means for enclosing.

16. The lancet device of claim 15 wherein said cap is integrally attached to said means for enclosing by a frangible connection so that twisting said cap relative to said means for enclosing causes said cap to become separated from said means for enclosing.

17. The lancet device of claim 1 further comprising a pair of finger pads attached to the outer surface of said means for connecting opposite said lancet needle to allow said means for connecting to be grasped and pinched between fingers of a user's hand towards said lancet needle.

18. The lancet device of claim 1 further comprising means for allowing said means for enclosing to easily move along said lancet needle as said means for connecting are moved toward each other.

19. The lancet device of claim 18 wherein said means for allowing comprises said lancet needle having a coating of a lubricous material along the length of said lancet needle that said means for enclosing traverses.

20. The lancet device of claim 18 wherein said means for allowing comprises said means for enclosing having a bore through which said lancet needle extends, said bore having a larger diameter than the diameter of said lancet needle.

21. A lancet device comprising:
a) a lancet needle having a distal and a proximal end, said proximal end of said lancet needle having a sharpened tip;
b) a distal needle piece enclosing said distal end of said lancet needle;
c) a proximal needle piece enclosing a portion of said lancet needle at said proximal end of said lancet needle; and
d) a pair of opposed normally bowed flexible arms connecting said distal needle piece to said proximal needle piece along opposite sides of said lancet needle, said arms having a center section between said distal needle piece and said proximal needle piece, said center section being relatively farther away from said lancet needle than the portions of said arms attached to said distal needle piece and attached to said proximal needle piece, said arms having a length, when bowed, to cause said sharpened tip to extend proximally beyond the proximal end of said means for enclosing, said arms having means, located at said center section, for receiving force directed toward said lancet needle, said arms having a rigidity so that as said arms are moved towards each other pressure is exerted by said arms on said distal needle piece and said proximal needle piece to move said proximal needle piece away from said distal needle piece along said lancet needle to a position to cover and enclose said lancet tip.

22. The lancet device of claim 21 wherein said proximal needle piece encloses said lancet needle along less of said lancet needle than said distal needle piece encloses said lancet needle.

23. The lancet device of claim 21 further comprising means for locking said proximal needle piece in a position covering and enclosing said lancet tip.

24. The lancet device of claim 23 wherein said means for locking includes said arms having at least one means for contacting said distal needle piece when said arms are moved toward said distal needle piece and said distal needle piece having means for retaining said means for contacting to lock said corresponding arms in contact with said distal needle piece thereby locking said proximal needle piece in position over said lancet tip.

25. The lancet device of claim 24 wherein said means for contacting comprises a protrusion extending from said arms towards said lancet needle and wherein said means for retaining includes said distal needle piece having a deformable recess in corresponding shape to said protrusion so that said protrusion is moved into said recess as said arms are moved toward said lancet needle and said recess deforms around said protrusion to retain said protrusion therein.

26. The lancet device of claim 23 wherein said means for locking includes said distal needle piece having at least one means for contacting said arms when said arms are moved toward said distal needle piece and said arms having means for retaining said means for contacting to lock said corresponding distal needle piece in contact with said arms thereby locking said proximal needle piece in position over said lancet tip.

27. The lancet device of claim 26 wherein said means for contacting comprises a protrusion extending from said distal needle piece away from said lancet needle and wherein said means for retaining includes said arms having a deformable recess in corresponding shape to said protrusion so that said protrusion is moved into said recess as said arms are moved toward said lancet needle and said recess deforms around said protrusion to retain said protrusion therein.

28. The lancet device of claim 21 further comprising a proximal finger pad attached to the proximal end of said proximal needle piece and a distal finger pad attached to said distal end of said distal needle piece.

29. The lancet device of claim 21 further comprising a removable cap encasing and enclosing said lancet tip.

30. The lancet device of claim 29 wherein said cap is integrally attached to said proximal needle piece.

31. The lancet device of claim 30 wherein said cap is integrally attached to said proximal needle piece by a frangible connection so that twisting said cap relative to said proximal needle piece causes said cap to become separated from said proximal needle piece.

32. The lancet device of claim 21 wherein said means for receiving force comprise a pair of finger pads attached to the outer surface of said arms at said center section opposite said lancet needle to allow said arms to be grasped and pinched between fingers of a user's hand towards said lancet needle.

33. The device of claim 2 wherein the axis of said arms is aligned parallel with the axis of said lancet needle.

34. The device of claim 2 wherein said arms are spaced around the axis of said lancet.

35. The device of claim 2 wherein said arms are resilient.

36. The device of claim 2 wherein said arms are one piece.

37. A lancet device comprising:

a) a lancet needle having a distal and a proximal end, said proximal end of said lancet needle having a sharpened tip;
b) means for enclosing a portion of said lancet needle at said proximal end of said lancet needle;
c) at least a pair of arms attached at one end to said distal end of said lancet needle and attached at an opposed end to said means for enclosing, said arms having a center section between said distal end of said lancet needle and said means for enclosing, said arms having a bowed shape in a relaxed condition so that said center section is relatively farther away from said lancet needle than the portions of said arms attached to said distal end of said lancet needle and attached to said means for enclosing, said arms, in said relaxed condition, having a length to cause said sharpened tip to be surrounded by said means for enclosing;
d) means, located at said center section, for receiving force applied to said center section directed toward said lancet needle; and,
e) a proximal finger pad attached to the proximal end of said means for enclosing and a distal finger pad attached to said distal end of said means for positioning;
whereby, as a user places a finger or thumb on said proximal finger pad and a finger or thumb on said distal finger pad and pinches the device, said arms deform into a more bowed configuration than is present when the device is not pinched and said sharpened tip extends through said means for enclosing into contact with the user's thumb or finger, thereby producing a drop of blood, and
whereby, as force is applied to said means for receiving force directed toward said lancet needle, said arms approach a straight shape as said center section is moved toward said lancet needle thereby extering pressure by said arms on said means for enclosing to move said means for enclosing away from said distal end of said lancet needle to a position to cover and enclose said lancet tip.

38. A lancet device comprising:
a) a lancet needle having a distal and a proximal end, said proximal end of said lancet needle having a sharpened tip;
b) means for enclosing a portion of said lancet needle at said proximal end of said lancet needle; and
c) at least a pair of one-piece arms attached at one end to said distal end of said lancet needle and attached at an opposed end to said means for enclosing, said arms being resilient over their entire length, said arms having a center section between said distal end of said lancet needle and said means for enclosing, said arms having a bowed shape in a relaxed condition so that said center section is relatively farther away from said lancet needle than the portions of said arms attached to said distal end of said lancet needle and attached to said means for enclosing, said arms, in said relaxed condition, having a length to cause said sharpened tip to extend proximally beyond the proximal end of said means for enclosing;
whereby said arms approach a straight shape as said center section is moved toward said lancet needle thereby exerting pressure by said arms on said means for enclosing to move said means for enclosing away from said distal end of said lancet needle to a position to cover and enclose said lancet tip.

39. In a lancet device having a lancet needle with a distal end and a sharpened proximal tip, a method for enclosing the sharpened proximal tip comprising the steps of:
a) enclosing a portion of the lancet needle at the proximal end of the lancet needle in a proximal needle piece; and
b) attaching a pair of arms to the distal end of the lancet needle and to said proximal needle piece, each of said arms having a center section between the distal end of the lancet needle and said proximal needle piece, each of said arms having a bowed shape in a relaxed condition so that said center section of each of said arms is relatively farther away from the lancet needle than the portions of said arms attached to the distal end of the lancet needle and attached to the proximal needle piece, said arms, in said relaxed condition, having a length to cause the sharpened tip to extend proximally beyond the proximal end of said proximal needle piece; and,
c) applying a force to said center sections to move said center sections toward the lancet needle, whereby said arms approach a straight configuration as said center sections are moved toward the lancet needle thereby exerting pressure by said arms on said proximal needle piece to move said proximal needle piece away from the distal end of the lancet needle to a position to cover and enclose the lancet proximal tip.

* * * * *